United States Patent
Nyberg et al.

(10) Patent No.: US 10,543,369 B2
(45) Date of Patent: Jan. 28, 2020

(54) ANTENNAS FOR USE WITH TRANSCUTANEOUSLY POWERED MEDICAL IMPLANTS

(71) Applicant: Advanced Bionics AG, Staefa (CH)

(72) Inventors: David André Nyberg, Frazier Park, CA (US); Markus Michael Heerlein, Valencia, CA (US); Jeryle L. Walter, Valencia, CA (US); Sung Jin Lee, Valencia, CA (US)

(73) Assignee: Advanced Bionics AG, Staefa (CH)

(*) Notice: Subject to any disclaimer, the term of this patent is extended or adjusted under 35 U.S.C. 154(b) by 185 days.

(21) Appl. No.: 15/561,038

(22) PCT Filed: Mar. 23, 2016

(86) PCT No.: PCT/US2016/023815
§ 371 (c)(1),
(2) Date: Sep. 23, 2017

(87) PCT Pub. No.: WO2016/171833
PCT Pub. Date: Oct. 27, 2016

(65) Prior Publication Data
US 2018/0071542 A1    Mar. 15, 2018

Related U.S. Application Data

(60) Provisional application No. 62/152,765, filed on Apr. 24, 2015.

(51) Int. Cl.
*A61N 1/372* (2006.01)
*H01F 27/28* (2006.01)
(Continued)

(52) U.S. Cl.
CPC ..... *A61N 1/37229* (2013.01); *H01F 27/2823* (2013.01); *H01Q 1/273* (2013.01);
(Continued)

(58) Field of Classification Search
CPC ................ A61N 1/37229; H01F 27/2823
(Continued)

(56) References Cited

U.S. PATENT DOCUMENTS

| 5,385,578 A | 1/1995 | Bush et al. |
| 7,191,007 B2 | 3/2007 | Desai et al. |

(Continued)

FOREIGN PATENT DOCUMENTS

WO    WO 2012/047550 A1    4/2012

OTHER PUBLICATIONS

PCT International Search and Written Opinion dated May 30, 2016 for PCT App. Ser. No. PCT/US2016/023815.
(Continued)

*Primary Examiner* — Nadia A Mahmood
(74) *Attorney, Agent, or Firm* — Henricks Slavin LLP

(57) ABSTRACT

An antenna having an inductor assembly including at least two conductors, which each define a conductor diameter $D_c$, and an electrically non-conductive carrier defining at least two lumens in which the at least two conductors are respectively located. The carrier maintains a conductor spacing S between the at least two conductors, and the inductor assembly defines at least one turn. The conductor spacing S and conductor diameter $D_c$ together define a $S/D_c$ ratio that ranges from about 0.5 to about 1.2.

15 Claims, 2 Drawing Sheets

(51) Int. Cl.
  *H01Q 1/27* (2006.01)
  *H01Q 7/00* (2006.01)
  *A61N 1/08* (2006.01)
  *A61N 1/378* (2006.01)
  *H01Q 7/06* (2006.01)

(52) U.S. Cl.
  CPC ............. *H01Q 7/00* (2013.01); *A61N 1/08* (2013.01); *A61N 1/3787* (2013.01); *H01Q 7/06* (2013.01)

(58) Field of Classification Search
  USPC ........................................................ 607/60
  See application file for complete search history.

(56) References Cited

U.S. PATENT DOCUMENTS

| | | |
|---|---|---|
| 7,876,282 B2 | 1/2011 | Keilman et al. |
| 8,781,606 B2 | 7/2014 | Keilman et al. |
| 2006/0038730 A1 | 2/2006 | Parsche |
| 2008/0051854 A1 | 2/2008 | Bulkes et al. |
| 2009/0248105 A1 | 10/2009 | Keilman et al. |
| 2010/0046779 A1 | 2/2010 | Crawford et al. |
| 2012/0089202 A1 | 4/2012 | Staller |
| 2014/0314264 A1 | 10/2014 | Meskins et al. |

OTHER PUBLICATIONS

Litz wire. In Wikipedia. Retrieved Apr. 17, 2015, from https://en.wikipedia.org/wiki/Litz_wire.
Litz Wire Types and Constructions. Retrieved Apr. 17, 2015, from www.newenglandwire.com.

ANTENNAS FOR USE WITH TRANSCUTANEOUSLY POWERED MEDICAL IMPLANTS

CROSS-REFERENCE TO RELATED APPLICATIONS

This application is the U.S. National Stage of PCT App. Ser. No. PCT/US2016/023815, filed Mar. 23, 2016, which claims priority to U.S. Prov. App. Ser. No. 62/152,765, filed Apr. 24, 2015.

BACKGROUND

1. Field

The present disclosure relates generally to transcutaneously powered medical implants.

2. Description of the Related Art

Inductive links are commonly used to transmit power and data to implanted medical devices such as, for example, prosthetic devices including cochlear implants and retinal implants, cardiac pacemakers, implantable defibrillators, recording devices, and neuromuscular stimulators. The implanted devices include (or are connected to) an internal antenna coil, and an external antenna coil is positioned over the internal antenna coil. Power and in some instances data is supplied to the implanted devices by way of the inductive link between the antenna coils.

In the exemplary context of implantable cochlear stimulation ("ICS") systems, which include an external sound processor as well as a cochlear implant with an electrode array within the cochlea, the external antenna coil may be carried by a headpiece that is connected to the external sound processor. The sound processor transmits power and stimulation data (e.g., a pulse sequence having varying pulse widths and/or amplitudes) through a power modulation scheme to the antenna coil of the cochlear implant by way of an inductive link. Electrical stimulation current is then applied to varying electrode combinations in the electrode array to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

One conventional antenna coil is a three turn inductor that includes a conductor within a non-conductive carrier. The conductor includes biocompatible multi-wire metal cables formed from gold, platinum or titanium wire. The cables are very small in diameter (e.g., about 0.014 inch) because the cochlear implant must be thin. Polyethylene reinforcing fibers are sometimes used to increase the tensile strength of the cables. The present inventors have determined that conventional antenna coils are susceptible to improvement. On the mechanical side, the thin multi-wire biocompatible metal cables are relatively expensive and complicated to manufacture, and also have relatively low tensile strength. Turning to electrical performance, the use of multi-wire biocompatible metal cables (and the polyethylene fiber) in antenna coils typically results in resistance values that are about one ohm or more and Q factor values that are less than 75, which is less than optimal for an implanted device.

SUMMARY

An antenna having an inductor assembly including at least two conductors, which each define a conductor diameter $D_C$, and an electrically non-conductive carrier defining at least two lumens in which the at least two conductors are respectively located. The carrier maintains a conductor spacing S between the at least two conductors, and the inductor assembly defines at least one turn but may present as many as required according to the design. The conductor spacing S and conductor diameter $D_C$ together define a $S/D_C$ ratio that ranges from about 0.5 to about 1.2.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
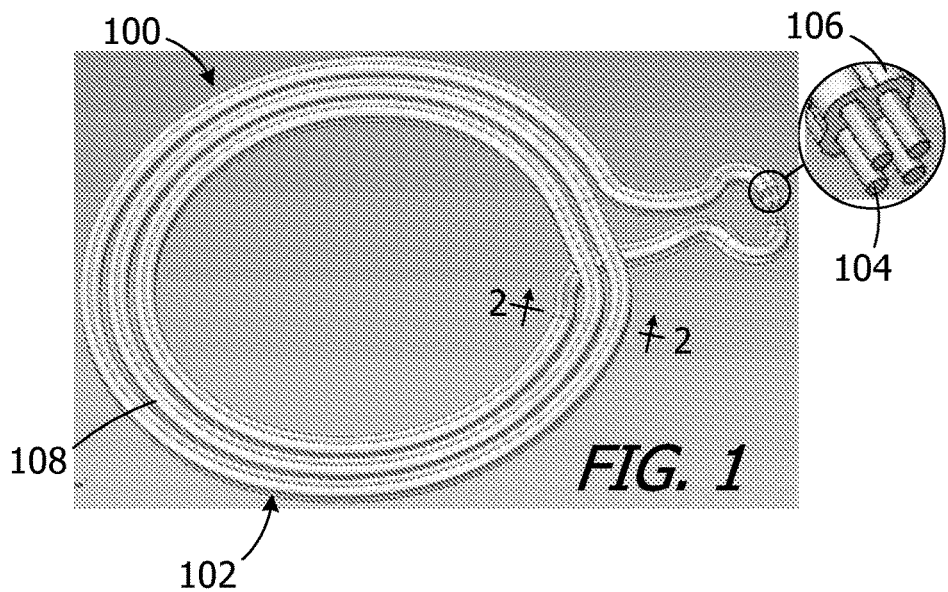
FIG. 1 is a perspective view of an antenna in accordance with one embodiment of a present invention.

One exemplary coil antenna is generally represented by reference numeral 100 in FIG. 1. The coil antenna 100 is formed by an inductor assembly 102 that includes a plurality of metallic conductors 104 which are positioned relative to one another such that there is a predetermined relationship between the conductor spacing and the conductor diameter, as is described in greater detail below. In the illustrated implementation, there are four metallic conductors 104 and the metallic conductors are located within a carrier 106 that maintains the position of the metallic conductors relative to one another. The ends of the metallic conductors 104 are exposed so as to facilitate connection to the receiver circuitry of the cochlear implant or other device. The metallic conductors 104 are described in greater detail below with reference to FIGS. 3 and 4. The inductor assembly 102 defines one or more turns (or "loops") 108, the number of which is determined by the intended application, and there are three turns in the illustrated embodiment.

Figure 2:
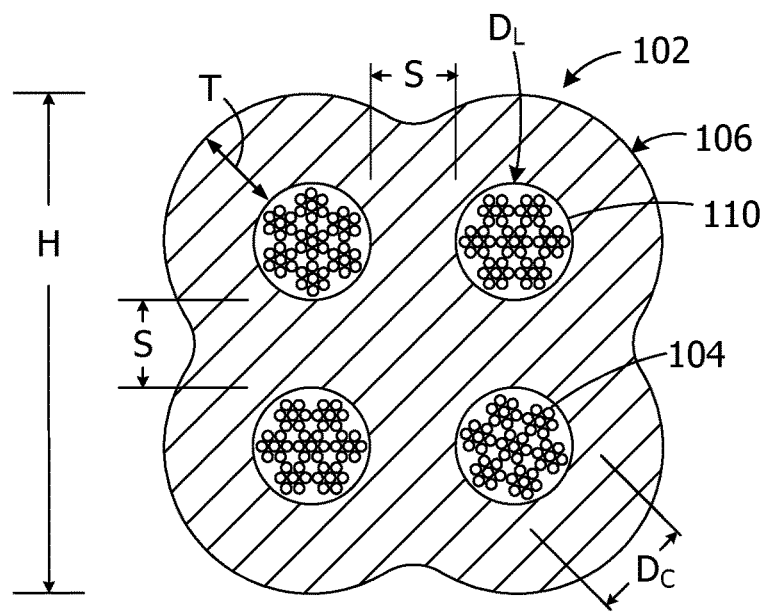
FIG. 2 is a section view of a single turn taken along line 2-2 in FIG. 1.
Figure 3:
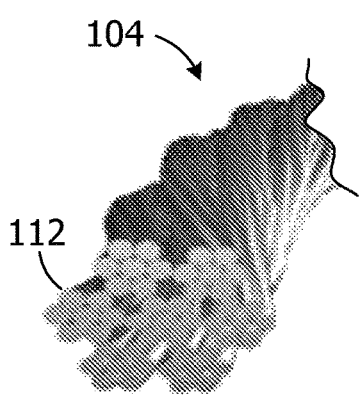
FIG. 3 is a perspective view of a portion of the antenna illustrated in FIG. 1.
Figure 4:
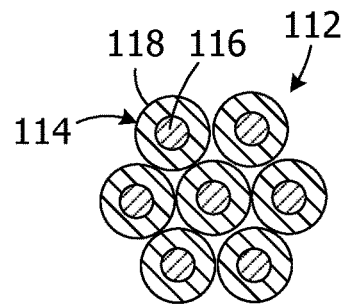
FIG. 4 is a section view of a portion of the antenna illustrated in FIG. 1.

As illustrated for example in FIG. 2, the exemplary carrier 106 includes a lumen 110 for each one of the metallic conductors 104. The carrier 106 may be formed from a dense elastomeric electrically non-conductive material such as silicone rubber. Turning to FIGS. 3 and 4, the conductors 104 may be formed from a plurality of multi-wire cables 112 (sometimes referred to as "Litz wires"). Each wire 114 in the cables 112 may be in the form of drawn filled tubing ("DFT"), available from Fort Wayne Metals as DFT® wire, that includes an outer tube 118 (e.g., an MP35N® nickel alloy tube) filled with an inner core 116 (e.g., a silver or silver alloy core). DFT is a registered trademark of Fort Wayne Metals Research Products Corp. and MP35N is a registered trademark of SPS Technologies. In the illustrated embodiment, the conductors 104 include seven multi-wire cables 112 that are arranged in a hexagonal formation where six of the cables 112 are twisted around a center cable. The cables 112 include seven wires 114 arranged in a hexagonal formation where six of the wires are twisted around a center wire. Such a configuration improves tensile strength as compared to conventional cables.

There are a number of advantages associated with the use of multi-cable conductors 104, as well as multi-wire cables 112, that have a Litz wire configuration. For example, the pattern into which the wires 114 are wound in the multi-wire conductors 104 reduces skin effect and proximity effect losses that occur in conductors carrying alternating current at radio frequencies. Briefly, the resistance of a wire carrying alternating current is a function of the cross-sectional area of the wire and the frequency of the current. The resistance increases as the cross-sectional area decreases. The resistance also increases as the frequency of the current increases because the effective cross-section area decreases due to the skin effect, which results in most of the current flow occurring near the surface of the wire. The individual wires 114 in the Litz cable configuration have diameters that are less than one skin depth, which eliminates the skin effect loss for each wire. Additionally, the radial location of each conductive wire 114 within a cable 112 (and of each cable 112 within a conductor 104) moves inwardly, where magnetic fields cause more resistance, and outwardly, where magnetic fields cause less resistance, along the length of the cable 112 (and conductor 104). As a result, the current is evenly distributed with a conductor 104 from wire 114 to wire 114 and from cable 112 to cable 112 and, for the conductor 104 as a whole, the skin effect and associated power losses are reduced in high-frequency applications. The ratio of distributed inductance to distributed resistance of a conductor 104 is also increased, relative to a solid conductor, which results in a higher Q factor at the resonant frequency. The Q factor is a unit-less indicator of efficiency, and a higher Q is indicative of a lower rate of energy loss for the conductor. In particular, $Q=\omega L/R$, where $\omega$=radian operating frequency, L=inductance and R=inductor's effective series resistance.

In addition to employing a multi-wire conductor such as those described above, simply increasing the cross-sectional area of the conductor is another method of decreasing series resistance to obtain a higher Q factor. The present inventors have, however, determined that increasing the cross-sectional area of the conductor is not an appropriate way to maximize Q factor in the context of implanted coil antennas due to the associated reduction in flexibility. The present inventors have also determined that a superior method of decreasing series resistance to obtain a higher Q factor is to form an antenna from a multi-cable inductor assembly such as the exemplary assembly illustrated in FIG. 2. The present inventors have further determined that there is a result-effective relationship between the conductor diameter and conductor spacing within the multi-cable inductor.

Referring again to FIG. 2, the conductors 104 define a maximum cross-section dimension and, because the twisting hexagonal shape of the conductors approximates a cylinder over their length, the maximum cross-section dimension of the conductors 104 is referred to herein and in the art as the diameter $D_C$. The four conductors 104 in the illustrated implementation are arranged two rows and two columns where pairs of conductors are horizontally and vertically aligned (in the illustrated orientation). There is a spacing S between vertically and horizontally aligned pairs of conductors 104. Put another way, the turns 108 define a loop plane that passes through the center of the carrier 106, and the conductors 104 are spaced parallel to the loop plane and perpendicular to the loop plane.

The present inventors have determined that the conductor spacing to conductor diameter ratio ("or $S/D_C$ ratio") should range from about 0.5 to about 1.2 and furthermore, spacing's that exceed a ratio of 1.2 fail to provide further benefit. The $S/D_C$ ratio is about 1.0 in the illustrated implementation. As used herein the context of the conductor spacing to conductor diameter ratio, the term "about" means±1%. The present inventors have determined that this relationship between the conductor spacing and conductor diameter reduces the proximity effect without creating parallel inductors. With respect to the proximity effect, when closely adjacent conductors are carrying alternating current, the distribution of current within the each conductor will be constrained by the magnetic field associated with the other conductor into a smaller region, thereby increasing the effective resistance in a manner that increases with the frequency of the current. In the present antenna 100, this problem cannot be solved by simply increasing the horizontal and vertical spacing between the conductors 104 because, at some point, the conductors will function as four parallel inductors instead of a single four cable inductor. Operation as four parallel inductors distorts the overall value of the final inductance and reduces the effect/benefit of the Litz effect. The present inventors have determined that, at a frequency within the range of 30 to 300 MHz (including, for example, the range of 45 to 55 MHz, and the exemplary value of 49 MHz), conductor spacing to conductor diameter ratios that range of from 0.5 to 1.2 maximizes the reduction in the proximity effect without creating parallel inductors.

In one exemplary implementation, the individual cable wires 114 consist of a silver alloy core 116 (at least 20% silver) and a nickel alloy tube 118, which provides both superior tensile strength and enhanced electrical conductivity. Each wire 114 has a diameter of about 0.001 inch. With six of the 0.001 inch wires 114 twisted around the center wire in the illustrated hexagonal formation to form the cables 112, and six of the cables 112 twisted around a center cable in the illustrated hexagonal formation to form the conductor 104, the diameter of the exemplary conductor is about 0.009 inch. As used herein the context of the diameters conductors 104 and wires 114, the term "about" means±0.001 inch. One commercially available multi-cable conductor that has the above-described configuration is available from Fort Wayne Metals, and comprises DFT® wire having an outer tube of MP35N® alloy and an inner core 116 of silver, with the silver core accounting for 28% of the cross sectional area of the wire.

The carrier 106, which as noted above may be formed from a dense elastomeric electrically non-conductive material such as silicone rubber, is configured to maintain the positions of the conductors 104 relative to one another. A suitable hardness is 60-80 shore A. In the illustrated implementation, each lumen 110 has a diameter $D_L$ of about 0.009 inch and the horizontal and vertical spacing S between adjacent lumens 110 is about 0.009 inch. The wall thickness T, which defines the distance between the conductors 104 and tissue, is also about 0.009 inch. As such, the total height H of the inductor assembly 102 is about 0.045 inch. The respective diameters of the three loops 108 in the illustrated embodiment are 0.8 inch, 0.9 inch and 1.0 inch. As used herein the context of the horizontal and vertical spacing S, the term "about" means±0.1%.

Figure 5:
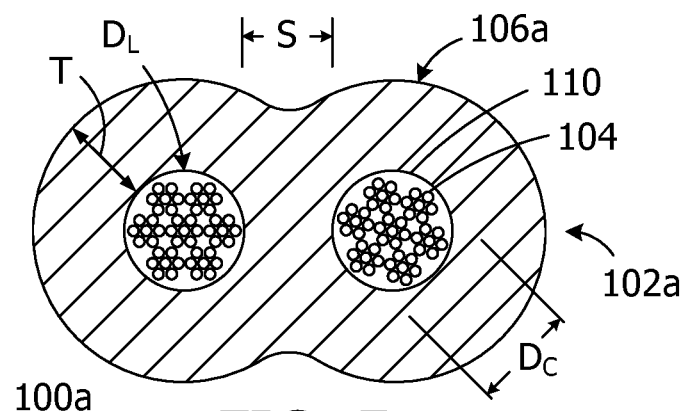
FIG. 5 is a section view of a portion of another antenna in accordance with one embodiment of a present invention.

It should also be noted that the present coil antennas are not limited to the four conductor implementation illustrated in FIGS. 1-4. Turning to FIG. 5, the illustrated antenna 100a is essentially identical to antenna 100 and similar elements are represented by similar reference numerals. Here, however, the inductor assembly 102a has only two conductors 104 and, accordingly, the carrier 106a includes only two lumens 110. The dimensions, conductor spacing and ratios discussed above are the same.

The present antennas have Q factor values that are a substantially better than those associated with antennas that have a similar overall configuration and a conventional conductor. By way of example, antennas 100 (FIGS. 1 and 2) and 100a (FIG. 5) may be compared to a conventional a three turn antenna that includes a conductor within a non-conductive carrier and which has the same overall size and shape. The conventional conductor includes four cables twisted around one another, with each cable including six gold wires twisted around a center wire to form the cable, and has a diameter of 0.012 inch. Antennas 100 and 100a were compared to the conventional antenna by measuring inductance L and effective series resistance R at particular frequencies and then calculating the Q value. The Q value of antenna 100 was about 65 percent higher than that of the conventional antenna, and the Q value of antenna 100a was about 30 percent higher than that of the conventional antenna. It should also be noted that the portion of the differences in Q values between the conventional antenna and the present antennas that can be attributed to the minor differences in wire material and cable configuration (i.e., the number of wires and diameter) is negligible.

Figure 6:
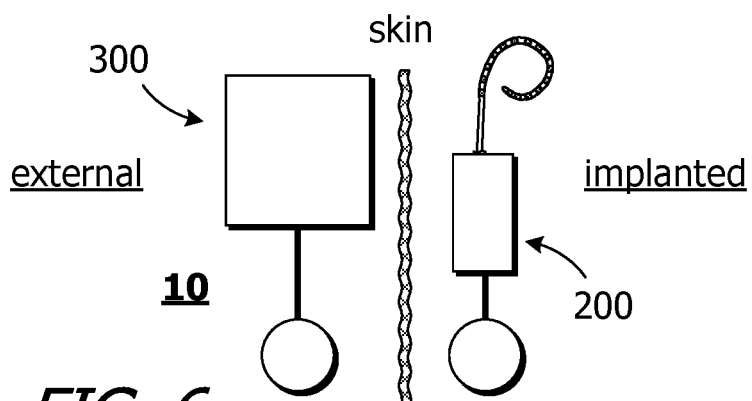
FIG. 6 is a diagrammatic view of an exemplary ICS system.

The present inventions have application in a wide variety of systems including, but not limited to, those that provide sound (i.e., either sound or a perception of sound) to the hearing impaired. One example of such a system is an ICS system where an external sound processor communicates with a cochlear implant and, accordingly, the present inventions may be discussed in the context of ICS systems. The present inventions are not, however, so limited. One example of an ICS system is the system generally represented by reference numeral 10 in FIG. 6. The exemplary ICS system 10 includes an implantable cochlear simulator (or "cochlear implant") 200 (FIG. 7) and sound processor 300 (FIG. 8).

Figure 7:
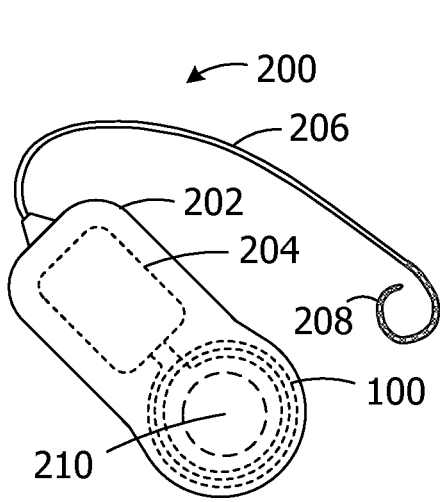
FIG. 7 is a plan view of an exemplary implantable cochlear stimulator.

The exemplary cochlear stimulator 200 illustrated in FIG. 7 includes a flexible housing 202 formed from a silicone elastomer or other suitable material, a stimulation processor 204, a cochlear lead 206 with an electrode array 208, and a positioning element (i.e., a magnet or other ferromagnetic material) 210. The cochlear stimulator 200 also includes data and power receiver apparatus which, in the illustrated implementation, consists of the above-described antenna 100 and a receiver (not shown). The stimulation processor 204 and receiver may be located on a common circuit board, or on separate boards.

Figure 8:
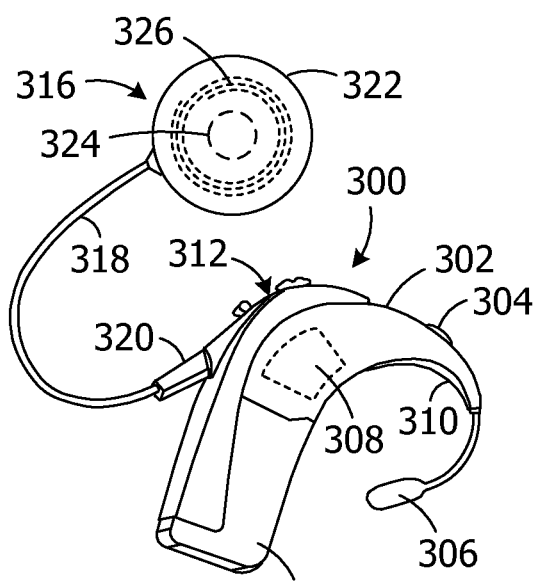
FIG. 8 is a perspective view of an exemplary sound processor.

Referring to FIG. 8, the exemplary sound processor 300 includes a housing 302, microphones 304 and 306, processor apparatus 308, and a retention member 310. The processor apparatus 308 may include any hardware, computer-implemented instructions (e.g., software), firmware, or combinations thereof. For example, the processor apparatus 308 may include one or more processors, digital signal processors ("DSPs"), filters, programmable memory units, and/or storage mediums. A control panel 312 that is positioned on the exterior of the housing 302 has a volume button and a program selector switch. The sound processor 300 also includes a primary or secondary battery or other power supply (not shown) that supplies power to the processor apparatus 308 and other power consuming components of the sound processor. In the illustrated implementation, the power supply is carried by a removable battery holder 314 that is secured to housing 302. A headpiece 316, which may be connected the sound processor 300 by way of a cable 318 and a cable port 320, includes a housing 322, a positioning magnet 324 that is attracted to the positioning element 210 of the cochlear stimulator 200, a coil antenna 326 (which is electrically similar to the antenna 100) and a transmitter (not shown). A wireless connection between the headpiece 300 and associated sound processor may be employed in other implementations. Power and stimulation data may be transcutaneously transmitted from the antenna 326 to the antenna 100 by way of an inductive link.

Although the inventions disclosed herein have been described in terms of the preferred embodiments above, numerous modifications and/or additions to the above-described preferred embodiments would be readily apparent to one skilled in the art. By way of example, but not limitation, the present inventions are applicable to ICS systems with body worn sound processors as well as BTE sound processors. The present inventions are also applicable to ICS systems with sound processor that communicate directly with the implantable cochlear stimulator by way of an internal antenna (i.e., without a headpiece) and sound processors wherein the sound processing and headpiece functionalities are incorporated into a single structure (see, e.g., U.S. Pat. Nos. 8,515,112 and 8,811,643, which are incorporated herein by reference). The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. An antenna for use with a medical implant, the antenna comprising:
    an inductor assembly including at least two conductors, which each define a conductor diameter $D_C$, and an electrically non-conductive carrier defining at least two lumens in which the at least two conductors are respectively located that maintains a conductor spacing S between the at least two conductors;
    wherein the inductor assembly defines at least one turn; and
    wherein the conductor spacing S and conductor diameter $D_C$ together define a $S/D_C$ ratio that ranges from about 0.5 to about 1.2.

2. An antenna as claimed in claim 1, wherein
    wherein the $S/D_C$ ratio is about 1.0.

3. An antenna as claimed in claim 1, wherein
the inductor assembly includes four conductors; and
the electrically non-conductive carrier defines four lumens in which the four conductors are respectively located.

4. An antenna as claimed in claim 3, wherein
the four conductors are arranged in two rows and two columns;
the $S/D_C$ ratio for the conductors in each row ranges from about 0.5 to about 1.2; and
the $S/D_C$ ratio for the conductors in each column ranges from about 0.5 to about 1.2.

5. An antenna as claimed in claim 1, wherein
each conductor includes six cables twisted around a center cable in a hexagonal formation.

6. An antenna as claimed in claim 5, wherein
each cable includes six wires twisted around an center wire in a hexagonal formation.

7. An antenna as claimed in claim 1, wherein
the inductor assembly defines three turns.

8. A cochlear implant, comprising:
a stimulation processor;
a cochlear lead with an electrode array operably connected to the stimulation processor; and
an antenna including
an inductor assembly with at least two conductors, which each define a conductor diameter $D_C$, and an electrically non-conductive carrier defining at least two lumens in which the at least two conductors are respectively located that maintains a conductor spacing S between the at least two conductors,
wherein the inductor assembly defines at least one turn, and
wherein the conductor spacing S and conductor diameter $D_C$ together define a $S/D_C$ ratio that ranges from about 0.5 to about 1.2.

9. A cochlear implant as claimed in claim 8, further comprising:
a flexible housing that houses the a stimulation processor and antenna.

10. A cochlear implant as claimed in claim 8, wherein
wherein the $S/D_C$ ratio is about 1.0.

11. A cochlear implant as claimed in claim 8, wherein
the inductor assembly includes four conductors; and
the electrically non-conductive carrier defines four lumens in which the four conductors are respectively located.

12. A cochlear implant as claimed in claim 11, wherein
the four conductors are arranged in two rows and two columns;
the $S/D_C$ ratio for the conductors in each row ranges from about 0.5 to about 1.2; and
the $S/D_C$ ratio for the conductors in each column ranges from about 0.5 to about 1.2.

13. A cochlear implant as claimed in claim 8, wherein
each conductor includes six cables twisted around a center cable in a hexagonal formation.

14. A cochlear implant as claimed in claim 13, wherein
each cable includes six wires twisted around an center wire in a hexagonal formation.

15. A cochlear implant as claimed in claim 8, wherein
the inductor assembly defines three turns.

\* \* \* \* \*